United States Patent [19]

Williams et al.

[11] Patent Number: 5,279,149

[45] Date of Patent: Jan. 18, 1994

[54] DIELECTRIC VISCOMETER INCLUDING FIXED AND VARIABLE CELLS

[75] Inventors: John G. Williams, Dollar Bay, Mich.; Thomas M. Donnellan, Huntington, N.Y.; Ronald E. Trabocco, Blue Bell, Pa.

[73] Assignee: The United States of America as represented by the Secretary of the Navy, Washington, D.C.

[21] Appl. No.: 902,138

[22] Filed: Jun. 22, 1992

Related U.S. Application Data

[63] Continuation-in-part of Ser. No. 629,299, Dec. 18, 1990, abandoned.

[51] Int. Cl.$^5$ ............................................. G01N 11/00
[52] U.S. Cl. ..................................................... 73/54.01
[58] Field of Search .......................... 73/54.01, 54.23

[56] References Cited

U.S. PATENT DOCUMENTS 3,864,961  2/1975  Cessna, Jr. .......................... 73/54.23

Primary Examiner—Hezron E. Williams
Attorney, Agent, or Firm—James V. Tura; James B. Bechtel; Susan E. Verona

[57] ABSTRACT

A parallel plate dielectric viscometer is provided for measuring the viscosity of a substance having differing substance dielectric properties at differing substance viscosities. Two electrodes are disposed in opposition to each other forming a variable dielectric cell having a dielectric distance between the electrodes. The viscosity of the substance is varied and force is applied to the substance to vary the dielectric distance according to the varying viscosity. The rate of change of the dielectric distance with respect to time is used to determine the viscosity of the substance. The viscosity may be varied by heating the substance and force may be applied to the substance by way of one of the electrodes such that the dielectric distance between the electrodes decreases as the substance becomes more viscous. A fixed cell may also be provided in order to correct for the effects of chemical changes in the substance.

14 Claims, 1 Drawing Sheet

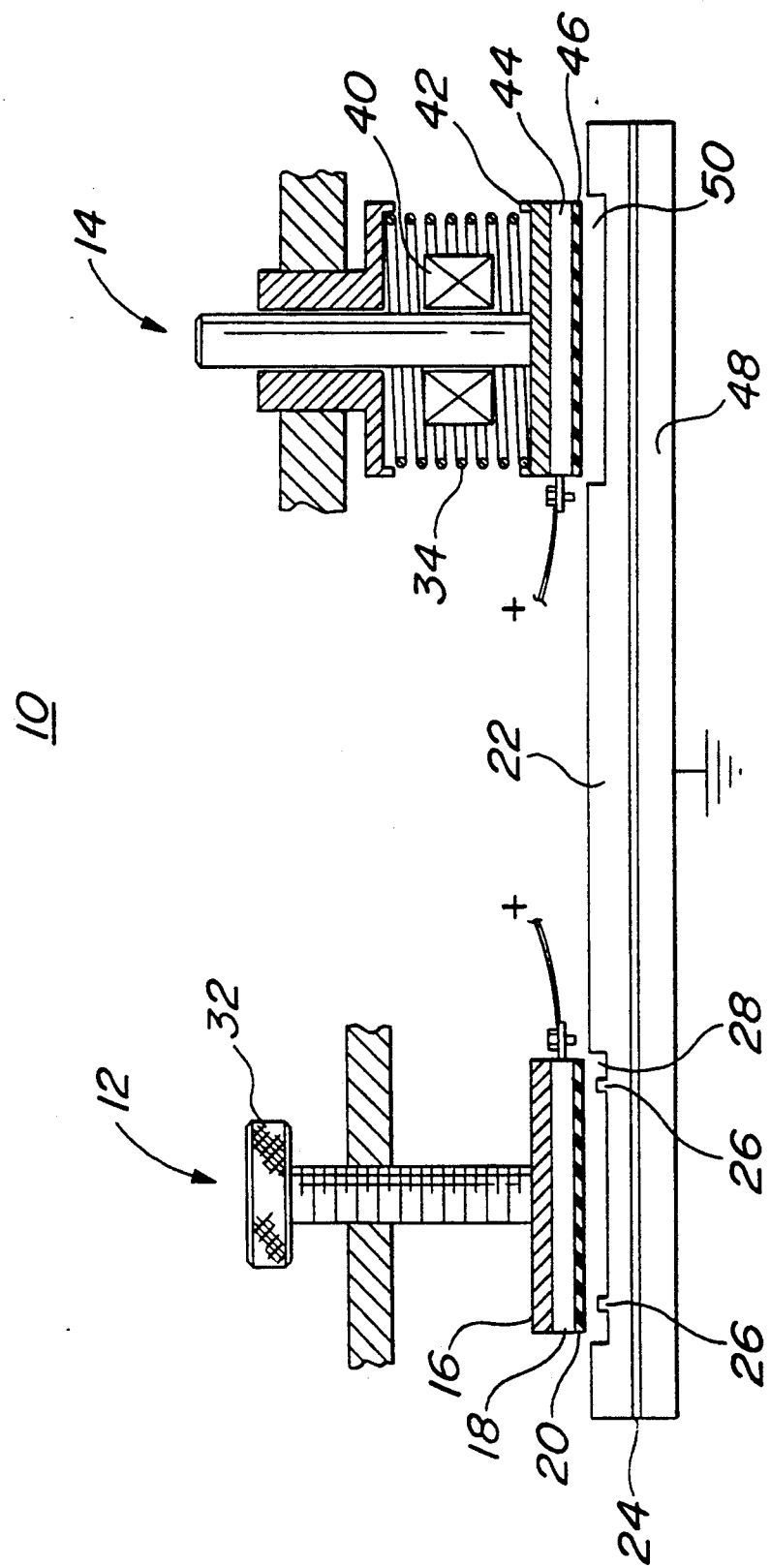

5,279,149

DIELECTRIC VISCOMETER INCLUDING FIXED AND VARIABLE CELLS

STATEMENT OF GOVERNMENT INTEREST

The invention described herein may be manufactured and used by or for the Government of the United States of America for governmental purposes without the payment of any royalties thereon or therefor.

This application is a continuation-in-part of copending application Ser. No. 07/629,299 filed Dec. 8, 1990 by John G. Williams et al. and now abandoned.

FIELD OF THE INVENTION

This invention relates to the field of viscometry and in particular to a dielectric viscometer for monitoring a multiphase substance using dielectric measurement.

BACKGROUND OF THE INVENTION

It is known in the art to use a capacitance probe to measure the dielectric constant of a liquid that occupies the space between plates of the probe. An alternating current signal is provided wherein the magnitude of the signal is proportional to the probe capacitance and thus to the value of the dielectric constant of the liquid. This alternating current signal is then processed with suitable circuitry to give an output signal representative of the liquid density.

U.S. Pat. No. 4,011,746, issued to Weit on Mar. 15, 1977, teaches a liquid density measurement system including such a capacitance probe. The probe is mounted for immersion in a mass of liquid, the density of which is to be measured. The capacitance of the probe depends on the dielectric constant of the liquid. A capacitance converter unit is connected to the probe and arranged to produce a signal which is dependent on the dielectric constant of the liquid. The system of Weitz is further provided with a temperature sensor also mounted for immersion in the liquid. A temperature signal conditioning unit is connected to the temperature sensor and adapted to provide a signal dependent upon the temperature of the liquid. A computation unit receives the two signals to produce an output signal proportional to the density of the liquid. Thus it is known in the art to compensate for temperature variation when using a capacitance probe to determine the dielectric constant of a liquid.

Additionally, the determination of dielectric constants of more viscous fluids is known. Some fluids may undergo a change in their dielectric properties as their viscosity changes thereby allowing a process accompanied by such changes to be monitored by capacitance probes. For example, dielectric properties are used in standard cure monitoring procedures and can be measured inside operating autoclaves. However, no adequate theoretical relationship has been determined between dielectric properties and rheological properties and viscometric properties. Such a theoretical relationship could be used for process control because the dielectric properties can be satisfactorily monitored during the cure process.

Thus it is difficult to determine the relationship between the deformability of the substance being cured or the ability of the substance being cured to flow, and the dielectric constant as measured by a capacitance probe. This is particularly true of multiphase systems where the proportion of material in each phase varies with time. In some pre-preg systems and in many adhesives, the matrix changes phase from liquid to gel to glass. Additionally, rubber particles may be precipitated during cure. Powder and fibrous fillers may be present. These fillers may flow with the matrix. Additionally, reinforcing fibers may be present. These reinforcing fibers remain stationary during resin flow. It is necessary to determine the viscosity profile of a resin being cured in a way which relates the viscosity profile directly to a dielectric profile representing capacitance and loss measurements. It is preferable that both measurements be determined simultaneously.

It is therefore an object of this invention to develop an instrument capable of accurate determination of the absolute viscosity of resin matrix materials and adhesives and its variation with time during resin cure cycles.

In particular, it is an object of the invention to monitor viscosity of isolated matrix resin, or unfilled adhesive.

A further object of the invention is to monitor the absolute or relative viscosity of matrix resin incorporated into a fiber bed or into pre-preg material and fiber-filled adhesive.

SUMMARY OF THE INVENTION

A parallel plate dielectric viscometer is provided for measuring the viscosity of a substance having differing substance dielectric properties at differing substance viscosities. Two electrodes are disposed in opposition to each other forming a variable dielectric cell having a dielectric distance between the electrodes. The viscosity of the substance is varied and force is applied to the substance to vary the dielectric distance according to the varying viscosity. The viscosity of the substance is determined according to the dielectric distance.

BRIEF DESCRIPTION OF THE DRAWING

The objects, advantages and novel features of the invention will become apparent from the following detailed description of the invention when considered in conjunction with the accompanying drawing wherein the parallel plate dielectric viscometer of the present invention is shown.

DETAILED DESCRIPTION OF THE INVENTION

Referring now to the drawing, parallel plate dielectric viscometer 10 of the present invention is shown. Parallel plate dielectric viscometer 10 is provided with a fixed cell 12 and a variable cell 14. Fixed cell 12 is provided with active electrode 18 for forming a fixed capacitance with common electrode plate 22. Electrode well 28 in common electrode plate 22 is provided for disposing active electrode 18 of fixed cell 12 within electrode well 28. Silicone rubber insulator 20 is disposed on the surface of active electrode 18 between active electrode 18 and the bottom of electrode well 28 in common electrode plate 22. A plurality of electrode well spacers 26 separate silicone rubber insulator 20, and thereby active electrode 18, from the bottom of electrode well 28 of common electrode 22. This separation between active electrode 18 and common electrode 22 permits a fluid (not shown) being monitored by dielectric viscometer 10 to pass between active electrode 18 and common electrode 22. Fixed cell 12 of parallel plate dielectric viscometer 10 is also provided with adjustable screw clamp 32 for calibrating fixed cell 12.

Adjustable screw clamp 32 is electrically decoupled from active electrode 18 of fixed cell 12 by insulator cap 16.

Variable cell 14 of parallel plate dielectric viscometer 10 includes movable active electrode 44. Movable active electrode 44 is provided with silicone rubber insulator 46 disposed upon the surface of movable active electrode 44 between movable active electrode 44 and common electrode 22. Movable active electrode 44, having silicone rubber insulator 46, is disposed in electrode well 50 of common electrode 22.

Heating element 24 is provided within parallel plate dielectric viscometer 10 between common electrode 22 and temperature control platen 48. Thus, common electrode 22 of parallel plate dielectric viscometer 10 may be substantially evenly heated to provide a substantially equal temperature within electrode well 28 of fixed cell 12 and electrode well 50 of variable cell 14. Temperature control platen 48 should be a non-ferro magnetic, mold released platen.

A resin rheology model may be used to define the flow of matrix resin in parallel plate dielectric viscometer 10. In the general case of two parallel circular plates of radius R separated a distance x by a fluid of viscosity $\eta$ and acted on by a uniform pressure P, the rate of change of cell spacing, dx/dt is given by:

$$\frac{dx}{dt} = \frac{2x^3 P}{3\eta R^2} \quad (1)$$

When parallel plate dielectric viscometer 10 is filled with an impregnated fiber bed of resin volume content $\epsilon$ and hydraulic radius m, the rate of change of bed thickness, dx/dt, is given by $$\frac{dx}{dt} = \frac{8P m^2 \epsilon x}{k\eta R^2} \frac{(\epsilon - \epsilon_{p\infty})(\epsilon_0 - \epsilon_\infty)}{(\epsilon_0 - \epsilon_{p\infty})(\epsilon - \epsilon_\infty)} \quad (2)$$

where $\epsilon_o$ is the resin volume fraction at zero pressure, $\epsilon_{P\infty}$ is the resin volume fraction at pressure P and fully compacted at time equal to infinity, and $\epsilon_{P\infty}$ the resin volume fraction fully compacted at infinite pressure.

In both cases the rate of change of the spacing of fixed cell 12 and variable cell 14 of parallel plate dielectric viscometer 10 is inversely proportional to the viscosity of the substance being cured. For unfilled fixed cell 12 and unfilled variable cell 14 the relationship is simple. But for fiber-bed filled cells 12, 14 the relationship depends strongly on the fiber component of the bed.

A simple method to monitor the spacing of cells 12, 14 is by determining the capacitance of cells 12, 14. This method assumes that cells 12, 14 do not conduct electricity and that the dielectric properties of a dielectric medium within electrode wells 28, 50 of cells 12, 14 are known. During the cure of matrix resins and adhesives, the dielectric properties of the medium vary and monitoring of the dielectric constant and loss is required in order to relate resin rheology and dielectric properties. In addition, it is very difficult to insure that active electrodes 18, 44 of cells 12, 14 do not make electrical contact with common electrode 22 at the small spacings required unless silicone rubber insulators 20, 46 are provided to isolate electrodes 18, 44 from the bottom of electrode wells 28, 50. If the fiber bed is based on carbon fibers, the problem is exacerbated by the conductive nature of the bed.

In the method of the present invention, the rheological and dielectric properties of the bed are determined from a comparison of fixed cell 12 and variable cell 14 filled with identical material. Fixed cell 12 is provided with a fixed and known cell spacing between active electrode 18 and common electrode 22 within electrode well 28. The spacing may be determined using adjustable screw clamp 32. Variable cell 14 is provided with an adjustable cell spacing between movable active electrode 44 and common electrode 22 within electrode well 50. Within variable cell 14 of parallel plate dielectric viscometer 10, common electrode 22 serves as a fixed electrode and active electrode 44 serves as a movable electrode capable of movement toward fixed electrode 22 at a constant and known pressure. Conventional capacitance bridges (not shown) may be used to monitor fixed cell 12 and variable cell 14 of parallel plate dielectric viscometer 10 simultaneously.

In parallel plate dielectric viscometer 10, or cell layout 10, movable active electrode 44 of variable cell 14 is ferromagnetic. Periodically the capacitance bridge for measuring the capacitance of variable cell 14 is disabled and electromagnet 40 of variable cell 14 is activated. When electromagnet 40 is activated, variable cell 14 is dilated. The electromagnetic field provided by electromagnet 40 is adapted to cause a small cyclic motion of moving electrode 44 toward and away from electrode 22 as moving electrode 44 approaches common electrode 22 under the influence of spring 34. This enables the rate of decrease of the spacing of variable cell 14 within electrode well 50 to be determined repeatably at the same spacing and resin content. This method would lead to possible errors due to volatilisation of impurities during the dilation. It is believed that this problem may be minimized by ensuring that the spacing of variable cell 14 is very small. In an alternate embodiment (not shown), movable active electrode 44 of variable cell 14 may be allowed to move in one direction only within electrode well 50. In this alternate embodiment, interpretation of results is more difficult for systems with fiber beds present.

In the preferred embodiment of parallel plate dielectric viscometer 10, dielectric cells 12, 14 may be provided with active electrodes 18, 44 having diameters of approximately fifty millimeters. At least one electrode 18, 22, 44 of each cell 12, 14 of parallel plate dielectric viscometer 10 is coated with silicone rubber film insulation such as insulators 20, 46 to provide a thin insulating film which has approximately constant dielectric properties over the temperature ranges covered. An alternative material may be a paraphenylene film or a very thin polyimide film. The thickness of insulators 20, 46 should be approximately the same so that the effect of insulators 20, 46 on dielectric measurements can be corrected more readily. Initially, dielectric capacitance cells 12, 14 are assembled without spacers 26 and without dielectric fluid. The capacitances of cells 12, 14 are trimmed electrically to give identical capacitance outputs and to thereby perform calibration of parallel plate dielectric viscometer 10.

Liquid resin or pre-preg (not shown) is then used to fill both fixed cell 12 and variable cell 14 of dielectric viscometer 10 so that fixed cell 12 is completely filled and compressed to a known thickness of dielectric material using a handpress (not shown) and spacers 26. Variable cell 14 or movable cell 14 is provided with a slightly higher resin content than fixed cell 12. When the spacing of variable cell 14 is approximately equal to the spacing of fixed cell 12, the pressure applied by adjustable pressurizing spring 34 of variable cell 14 should be known. This known pressure should be of a magnitude which causes consolidation of the bed at a reasonable rate. The magnitude of the pressure may be adjusted using an adjustable screw (not shown) which bears on adjustable pressurizing spring 34 or by the use of differing adjustable pressurizing springs 34. It will be understood by those skilled in the art that the function as of pressurizing springs 34 may be performed by an electric motor (not shown) or a ferromagnetic device (not shown).

The capacitances of fixed cell 12 and variable cell 14 are monitored continuously using, for example, an Audrey dielectric spectrometer (not shown), at fixed frequencies. The values of the capacitances of dielectric cells 12, 14 are compared and the rate of change of capacitance of variable cell 14 is determined. At the moment the two capacitances are the same, the value of the capacitance, the dielectric loss, the temperature and time are recorded. It will be understood by those skilled in the art that a brief pause is associated with accurate techniques of measurement of the rate of change of capacitance within cells 12, 14. After this pause the capacitance meters are momentarily disabled and electromagnet 40 of variable cell 14 is enabled. Capacitance is then monitored approximately until a finitely lower capacitance is obtained in moving cell 14. The capacitance measurement device and electromagnet 40 are again momentarily disabled. Capacitance is then monitored accurately and the cycle is repeated.

The system of the present invention may be controlled by a microprocessor (not shown) to allow manipulation of the data in order to determine and output the required information. During heat-up of parallel plate dielectric viscometer 10 by means of heater element 24, a determination may be made of the capacitance and capacitive loss of dielectric cells 12, 14 and the rate of change of capacitance with time within variable cell 14. It is assumed that the rate of change of capacitance of stationary cell 12 or fixed cell 12 due to the polymerization of the resin is small over the time period of a single cycle.

The manipulations of the data required may be carried out by conventional digital or analog techniques. Using these techniques, a determination is made at each cycle with respect to resin viscosity, fluidity, time-integral fluidity, resin dielectric constant, loss factor, temperature and time. These variables may be plotted on appropriate linear or logarithmic scales covering all or part of the experimental procedure. In addition to the required viscometric and dielectric data, of particular use are curves of integral-fluidity against time during cure of the resin. This is the required processing information and dielectric loss against temperature during subsequent cooling down of the fixed cell 12 and variable cell 14. This latter measurement has a major peak at the glass transition temperature. A sample removed from fixed cell 12 should be fully cured material of constant thickness and should be useable for interlaminar shear tests of dynamic mechanical analysis using an analyzer such as a 1090 Thermal Analyzer 982 DMA Instrument (not shown).

Active electrodes 18, 44 of capacitive cells 12, 14 of parallel plate dielectric viscometer 10 have the same surface area. Silicone rubber insulators 20, 46 disposed upon active electrodes 18, 44 are formed of similar but not identical thickness. A series trim capacitor (not shown) having a capacitance $C_t$ is inserted in line with fixed capacitor cell 12 which has a capacitance $C_{f,t}$. The trimming capacitor is then trimmed. Trimming is performed such that the total capacitance of the trim capacitor and fixed cell 12 is identical to that of variable cell 14 when both capacitive cells 12, 14 are closed to the thickness of insulating films 20, 46. The capacitance of variable cell 14 is $C_{v,t}$.

$$\frac{1}{C_{v,o}} = \frac{1}{C_{f,o}} + \frac{1}{C_t}$$

$$\therefore \frac{1}{C_{v,o}} = \frac{1}{C_t} + \frac{4\pi x_{f,o}}{AE_o} = \frac{4\pi x_{v,o}}{AE_o}$$

$$\therefore \frac{1}{C_t} = 4\frac{\pi}{AE_o}(x_{v,o} - x_{f,o}),$$

where A represents the area and $E_o$ represents the dielectric constant. Using the initial set up, the value of $C_{v,o}$ is recorded in the memory processor controlling the system of parallel plate dielectric viscometer 10.

During operation of parallel plate dielectric viscometer 10 the thermal energy applied to dielectric viscometer 10 causes the substance being monitored between plates 22, 44 of variable cell 14 to soften. This permits moving plate 44 to advance toward common plate 22 under the influence of spring 34. During the time that the dielectric distance between plate 44 and plate 22 decreases, the rate of change of $1/C_{v,t}$ with respect to time is determined $(d(1/C_{v,t})/dt)$. Additionally, the absolute magnitude of $C_{v,t}$ and the series sum of $C_T$ and $C_{s,t}$ are compared. At the point when $C_{v,t}$ is equal to this sum a record is made of $d(1/C_{v,t})/dt$, $C_{v,t}$, the loss in $C_{v,t}$, the temperature, and the elapsed time. At that time, when the capacitances are equal, the following identity is true:

$$\frac{1}{C_{v,t}} = \frac{1}{C_{f,t}} + \frac{1}{C_t}$$

as $$\frac{1}{C_{v,t}} = \frac{4\pi x_{v,t}}{AE_{v,t}} + \frac{4\pi x_{v,o}}{AE_o}$$

$$\frac{1}{C_{f,t}} = \frac{4\pi x_{f,t}}{AE_{f,t}} + \frac{4\pi x_{f,o}}{AE_o}$$

$$\therefore \frac{X_{v,t}}{E_{v,t}} = \frac{X_{f,t}}{E_{f,t}}$$

The rate of change of $C_{v,t}$ $(d(1/C_{v,t})/dt)$ is obtained by differentiation. In this difference, only $x_t$ and $E_t$ vary with time.

$$\frac{d(1/C_{v,t})}{dt} = \frac{d}{dt}\left(\frac{4\pi x_{v,t}}{AE_{v,t}}\right)$$

Using standard rules of differentiation of a ratio:

$$\frac{d(1/C_{v,t})}{dt} = \frac{4\pi}{A} \frac{\left[E_{v,t}\frac{dx_{v,t}}{dt} - x_{v,t}\frac{dE_{v,t}}{dt}\right]}{E_{v,t}^2}$$

If the rate of change of $E_t$ is small in any one measurement:

$$\frac{X_{v,t}}{dt} > \frac{E_{v,t}}{dt}$$

-continued $$\frac{d(1/C_{v,t})}{dt} = \frac{4\pi}{AE_{v,t}} \left[ \frac{dx_{v,t}}{dt} \right]$$

Also monitored continuously is $C_{f,t}$. This value can readily be corrected for the value of $C_{f,o}$ to give the difference $$\frac{1}{C_{f,t}} - \frac{1}{C_{f,o}}.$$

This difference can be expressed as:

$$\frac{1}{C_{f,t}} - \frac{1}{C_{f,o}} = \frac{4\pi x_{f,t}}{AE_{f,t}} = \frac{4\pi x_{v,t}}{AE_{v,t}}$$

The ratio $d(1/C_{v,t})/dt$ divided by $(1/C_{f,t}-1/C_{f,o})$ is B and the value of B is given by:

$$B = \frac{\frac{d(1/C_{v,t})}{dt}}{1/C_{v,t} - 1/C_{v,o}} = \frac{dx_{v,t}/dt}{x_{v,t}}$$

For a liquid filled capacitive cell 12, 14 within parallel plate dielectric viscometer 10:

$$\frac{dx}{dt} = \frac{2x^3 P}{3\eta R^2}$$

the value for the viscosity $\eta$ is given by:

$$\eta = \frac{1}{B} \frac{2x^2 P}{3R^2}$$

Similarly for a composite filled cell within viscometer 10

$$\eta = \frac{1}{B} \left[ \frac{8Pm^2\epsilon}{kR^2} \frac{(\epsilon - \epsilon_{p,\infty})(\epsilon_o - \epsilon_\infty)}{(\epsilon_o - \epsilon_{p,m})(\epsilon - \epsilon_\infty)} \right]$$

All of the constants in these expressions must be known for the analysis of resin rheology using parallel plate dielectric viscometer 10 of the present invention. Calculated values can be used to obtain absolute values for the viscosity.

In some cases, it may be better to calibrate fixed cell 12 and variable cell 14 of parallel plate dielectric viscometer 10 using fluids of known viscosity. Some problems may be experienced in the values for the bed constants, for example, M, $\epsilon_o$, $\epsilon_{P\leq}$, $\epsilon_{23}$ and flow constant, k, which may be dependent on the fluid used in their measurement.

Once a value is obtained for the viscosity, the fluidity and time integral fluidity are readily determined. The dielectric properties for dielectric cells 12, 14, corrected for insulating layers 20, 46, are determined during the operation of parallel plate dielectric viscometer 10 $(1/C_{v,t}-1/C_{v,o})$. Dielectric loss may be monitored independently throughout the operation.

Thus, as the cure process monitored by parallel plate dielectric viscometer 10 proceeds, two parameters change. The spacing between electrodes 22, 44 of variable dielectric cell 14 changes due to the force applied by spring 34 by way of moving electrode 44 upon the substance whose viscosity is changing due to the application of thermal energy. This factor is influenced by how the resin flows under the influence of pressure. Additionally, the change in the cure state of the substance being monitored and the resulting chemical changes in the substance alter the dielectric constant measured in dielectric variable cell 14. Fixed cell 12 therefore provides an estimate of this change due to the change in chemistry of the substance. In order to perform a correction, the effect on fixed cell 12 is subtracted from the measurement of variable cell 14 in order to isolate the effect of the change of distance.

Many modifications and variations of the present invention are possible in view of the above disclosure. It is therefore to be understood, that within the scope of the appended claims, the invention may be practiced otherwise than as specifically described.

We claim:

1. A parallel plate dielectric viscometer for measuring the viscosity of a substance having differing substance dielectric properties at differing substance viscosities, comprising:

first and second electrode means disposed in opposition to each other forming a variable dielectric cell having a dielectric cell distance between said first and second electrode means;

means for disposing said substance between said opposed first and second electrode means;

means for varying said substance viscosity;

means for applying force to said substance to vary said dielectric distance in accordance with said varying substance viscosity;

means for determining the rate of change of said dielectric distance;

third and fourth electrode means forming a fixed dielectric cell having a fixed dielectric cell distance between said third and fourth electrode means;

means for determining a first dielectric constant between said first and second electrode means;

means for determining a second dielectric constant between said third and fourth electrode means; and, said means for determining said substance viscosity being adapted to determine said substance viscosity in accordance said first and second dielectric constants.

2. The parallel plate dielectric viscometer of claim 1, wherein said means for varying the substance viscosity comprises a source of thermal energy.

3. The parallel plate dielectric viscometer of claim 1, wherein said means for applying force comprises electromagnetic means.

4. The parallel plate dielectric viscometer of claim 1, wherein said means to apply force comprises an electric motor.

5. The parallel plate dielectric viscometer of claim 1, wherein said means for applying force to said substance comprises means for applying force by way of at least one of said first and second electrode means.

6. The parallel plate dielectric viscometer of claim 5, wherein said means for applying force comprises biasing means.

7. The parallel plate dielectric viscometer of claim 6, wherein said biasing means is adapted to bias said first electrode means toward said second electrode means.

8. The parallel plate dielectric viscometer of claim 1, further comprising means to dilate said dielectric cell.

9. The parallel plate dielectric viscometer of claim 1, wherein at least one of said first and second electrode means is formed of a ferromagnetic material, further comprising electromagnetic means for providing dilation of said variable dielectric cell.

10. The parallel plate dielectric viscometer of claim 9, wherein said electromagnetic means is adapted to provide cyclic motion to said ferromagnetic electrode means.

11. A method of determining the substance viscosity of a substance having differing dielectric properties at differing substance viscosities, comprising the steps of:
 (a) providing opposed first and second electrode means separated by a dielectric distance to form a variable dielectric cell;
 (b) disposing said substance between said first and second electrode means;
 (c) varying said substance viscosity;
 (d) applying force to said substance to vary said dielectric distance in accordance with said substance viscosity;
 (e) determining said dielectric distance between said first and second electrode means;
 (f) determining said substance viscosity in accordance with the rate of change of said dielectric distance;
 (g) providing a fixed dielectric cell having third and fourth electrode means and a fixed dielectric distance between said third and fourth electrode means;
 (h) determining a first dielectric constant between said first and second electrode means;
 (i) determining a second dielectric constant between said third and fourth electrode means; and,
 (j) determining said substance viscosity in accordance with said first and second dielectric constants.

12. The method of determining the viscosity of a substance of claim 11, wherein step (c) comprises applying thermal energy to said substance.

13. The method of determining the viscosity of a substance of claim 11, wherein at least one of said first and second electrode means is formed of a ferromagnetic substance, comprising the further step of dilating said variable dielectric cell by means of electromagnetic means.

14. The method of determining the viscosity of a substance of claim 13, comprising the further step of providing cyclic motion to said ferromagnetic electrode means by means of said electromagnetic means.

* * * * *